(12) United States Patent
Vermeiren et al.

(10) Patent No.: US 9,115,040 B2
(45) Date of Patent: Aug. 25, 2015

(54) PRODUCTION OF ISOPRENE FROM ISO-BUTANOL

(75) Inventors: Walter Vermeiren, Houthalen (BE); José Castor Gonzalez, Jette (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 135 days.

(21) Appl. No.: 13/825,749

(22) PCT Filed: Sep. 6, 2011

(86) PCT No.: PCT/EP2011/065350
§ 371 (c)(1),
(2), (4) Date: Apr. 26, 2013

(87) PCT Pub. No.: WO2012/038247
PCT Pub. Date: Mar. 29, 2012

(65) Prior Publication Data
US 2013/0217942 A1  Aug. 22, 2013

(30) Foreign Application Priority Data
Sep. 24, 2010 (EP) .................... 10179213

(51) Int. Cl.
*C07C 1/22* (2006.01)
*C07C 1/24* (2006.01)
*C07C 2/86* (2006.01)

(52) U.S. Cl.
CPC ... *C07C 1/22* (2013.01); *C07C 1/24* (2013.01); *C07C 2/867* (2013.01)

(58) Field of Classification Search
None
See application file for complete search history.

(56) References Cited

U.S. PATENT DOCUMENTS

| | | | |
|---|---|---|---|
| 3,972,955 A | 8/1976 | Halcour et al. | |
| 4,511,751 A | 4/1985 | Ninagawa et al. | |
| 4,593,145 A | 6/1986 | Ninagawa et al. | |
| 2007/0106104 A1 | 5/2007 | Yamada et al. | |
| 2008/0031981 A1 | 2/2008 | Du Pont et al. | |
| 2008/0261230 A1 | 10/2008 | Liao et al. | |
| 2010/0216958 A1 | 8/2010 | Peters et al. | |

FOREIGN PATENT DOCUMENTS

| | | |
|---|---|---|
| EP | 106323 A1 | 4/1984 |
| EP | 2157072 A1 | 2/2010 |
| GB | 1370899 A | 10/1974 |

OTHER PUBLICATIONS

Atsumi, Shota et al. "Non-fermentative pathways for synthesis of branched-chain higher alcohols as biofuels" • Nature, 451, 2008. p. 86.
Olson, Edwin S. et al. "Highter-Alcohols Biorefinery: Improvement of Catalyst for Ethanol Conversion." Applied Biochemistry and Biotechnology, 113-116, 2004, p. 913.

*Primary Examiner* — In Suk Bullock
*Assistant Examiner* — Sharon Pregler

(57) ABSTRACT

The present invention is a process to make isoprene comprising:
a) providing a reaction zone comprising an acidic aqueous solution,
b) introducing, continuously or intermittently, in said reaction zone
a mixture comprising (i) isobutanol and optionally (ii) t-butanol or an iso-butene precursor which is not isobutanol and not t-butanol or iso-butene or any combination of two or three of these (ii) components,
an aqueous solution of formaldehyde,
c) operating said reaction zone at conditions effective to dehydrate isobutanol and optionally (ii) t-butanol and optionally the iso-butene precursor to iso-butene and produce isoprene by reaction of formaldehyde and iso-butene while distilling away a mixture comprising produced isoprene, water, unreacted starting materials and other low boiling point components from this reaction zone to the outside of the reaction zone.
In another embodiment isobutanol provides 10% or more of the iso-butene for the isoprene synthesis.
In another embodiment isobutanol provides 20% or more of the iso-butene for the isoprene synthesis.
In another embodiment isobutanol provides 30% or more of the iso-butene for the isoprene synthesis.
In another embodiment isobutanol provides 40% or more of the iso-butene for the isoprene synthesis.
In another embodiment isobutanol provides 50% to 100% of the iso-butene for the isoprene synthesis.

19 Claims, No Drawings

PRODUCTION OF ISOPRENE FROM ISO-BUTANOL

CROSS-REFERENCE TO RELATED APPLICATIONS

This application claims the benefit of PCT/EP2011/065350, filed Sep. 6, 2011, which claims priority from EP 10179213.3, filed Sep. 24, 2010.

FIELD OF THE INVENTION

The present invention relates to a process for producing isoprene from iso-butanol, preferably obtained from renewable resources. Isoprene is used as a basic chemical starting material for various chemical products and elastomers. The limited supply and increasing cost of crude oil has prompted the search for alternative processes for producing hydrocarbon products such as isoprene. Iso-butanol can be obtained by fermentation of carbohydrates or by condensation of lighter alcohols, obtained by fermentation of carbohydrates. Made up of organic matter from living organisms, biomass is the world's leading renewable energy source.

BACKGROUND OF THE INVENTION

Conventionally isoprene is produced by extraction from pyrolysis gasoline, which is a byproduct of steamcracking of naphtha. The yield is typically very low, of the order of 1-3% of the produced ethylene. Hence it is difficult to justify this capital-intensive technology for only a small production capacity of isoprene. The process to isolate isoprene from pyrolysis gasoline consist first in the removal of cyclopentadiene by dimerisation and distillation. Next the pipirylenes are separated by superfractionation. The last steps consist in an extractive distillation using a solvent. Moreover the quality of isoprene obtained from pyrolysis gasoline is hard to guarantee as the specifications with respect to cyclopentadiene and pipirylenes are very severe and these compounds are plentiful present in the same pyrolysis gasoline. As pyrolysis gasoline contains only small amounts of isoprene (10-20%), a lot of byproducts (dicyclopentadiene and pipirylene) are produced according to the same laborious manner while their market value is not necessary in line with the evolution of the market value of isoprene.

Recently, there is a tendency to shift to lighter feedstock for steamcracking feeding. Most new steamcrackers are using ethane as feedstock that does not produce pyrolysis gasoline as byproduct. Also many naphtha-based steamcrackers are shifting to lighter feedstock because of its abundant availability and competitive advantage.

Other routes to produce isoprene are the isolation of isoamylenes from refinery and petrochemical cuts and perform a dehydrogenation into isoprene. This process is typically done over iron oxide catalyst promoted with potassium compounds at temperatures above 600° C. in presence of water steam and reduced pressure. As this reaction is limited by a thermodynamic equilibrium, only partial conversions can be obtained.

Isoprene can also be produced from isopentane by a double dehydrogenation.

In still another process, isoprene is produced by a two-step process. In the first step iso-butene, tertiary-butanol, di-t-butyl ether, methyl-t-butyl ether or ethyl-t-butyl ether is condensed with two molecules of formaldehyde to form dimethyloxirane. The dimethyloxirane is separated and purified. In the second step the dimethyloxirane is decomposed under appropriate conditions into isoprene and one molecule of formaldehyde. An improvement on the latter two-step process, in which iso-butene, tertiary-butanol, di-t-butyl ether, methyl-t-butyl ether or ethyl-t-butyl ether is directly reacted with formaldehyde into isoprene.

The U.S. Pat. No. 4,511,751 describes a process for producing isoprene in good yield. The process is characterized in that iso-butene and/or tertiary butanol and a formaldehyde source are fed, together with water, into an acidic aqueous solution continuously or intermittently while maintaining the reaction pressure in an adequate range and at the same time distilling off the product isoprene and unreacted starting materials, together with water, from the reaction zone.

The U.S. Pat. No. 4,593,145 describes a process for producing isoprene, characterized in that an alkyl-t-butyl ether and a formaldehyde source are fed, together with water, into an acidic aqueous solution continuously or intermittently while maintaining the reaction pressure in an adequate range and at the same time distilling off the product isoprene, unreacted starting materials, iso-butene and tertiary butanol, together with water, from the reaction zone.

EP106323 describes a process for producing isoprene by reacting iso-butene and/or tertiary butanol and/or an alkyl tertiary butyl ether which gives iso-butene and/or tertiary butanol under the reaction conditions with formaldehyde in an acidic aqueous solution, under such conditions (a) that the acidic aqueous solution is present in the reaction zone, (b) that iso-butene and/or tertiary butanol and/or the alkyl tertiary butyl ether, a formaldehyde source and water are fed to said reaction zone continuously or intermittently, and (c) that isoprene, water, unreacted starting materials and other low-boiling components are distilled off from said reaction zone, wherein a glycol ether is added, in an amount of 5 to 15 percent by weight, to the acid aqueous solution. It is specified that the presence of a solvent in the reactor improves the solubility of iso-butene in the aqueous phase and hence the contact with the acid catalyst that is substantially dissolved in the aqueous solution.

EP 1 614 671 A1 describes process for producing isoprene, which includes continuously or intermittently supplying iso-butene and/or t-butanol, formaldehyde and water into an acidic aqueous solution, and reacting the reaction mixture while distilling away a mixture containing produced isoprene, water, unreacted starting materials and other low boiling point components from this reaction mixture to the outside of the reaction system, wherein the reaction is carried out while controlling the concentration of high boiling point byproducts, which is produced and accumulated in the reaction mixture, to fall within the range of 0.5-40 mass %.

EP 2 157 072 A1 describes a method to obtain isoprene by way of liquid-phase interaction between trimethyl carbinol (also known as t-butanol, or its water solutions) and formaldehyde (or its source substances) in the presence of acidic catalyzer water solution; this can be made in one or several contacting stages, with use (at the final contacting stage) of separation reactor containing a heat supply zone, a reaction zone and a separation zone, with reaction products and water taken, out of the separation zone, in the form of a vapor flow to be subsequently cooled down, condensed and separated and with liquid flow of the catalyzer water solution put out for extraction and, after this, put back into the heating zone. As it goes from the reaction zone into the separation zone, the reactive flow is throttled. In the reaction zone, temperature is maintained at the level of 140-180° C., while pressure is 8-25 atmospheres; in the separation zone, pressure is 1.2-9.5 atmospheres. The separation reactor contains two or three separation zones. The balance quantity of water is put out of catalyzer water solution, which is circulating along the circuit, by way of its evaporation as the flow is throttled into the separation zone (zones) during regulation of the quantity of the circulating liquid phase in the interval of 0.2-6.0 parts of the total reaction zone area.

US 2010 0216958 A1 relates, in one embodiment, to a method of preparing butadiene comprising (a) providing an alcohol mixture comprising one or more butanols; (b) contacting the alcohol mixture with a dehydration catalyst, thereby forming an olefin mixture comprising one or more linear butenes and isobutene; (c) contacting the olefin mixture of step (b) with a dehydrogenation catalyst, thereby forming a di-olefin mixture comprising butadiene and isobutene; and (d) isolating butadiene from the di-olefin mixture of (c).

In another embodiment, it relates to a method of preparing isoprene comprising (a) providing an olefin mixture comprising one or more pentenes, with the proviso that at least a portion of the olefin mixture comprises one or more methylbutenes; (b) contacting the olefin mixture of (a) with a dehydrogenation catalyst, thereby forming a mixture comprising isoprene; and (c) isolating isoprene from the mixture of (b).

In still another embodiment, it relates to a method of preparing monomers, comprising: (a) providing an olefin mixture comprising one or more linear butenes and isobutene; (b) contacting the olefin mixture of step (a) with a dehydrogenation catalyst, thereby forming a di-olefin mixture comprising butadiene and isobutene; (c) isolating isobutene from the mixture of step (b); and (d1)) converting the isobutene to methyl t-butyl ether, ethyl t-butyl ether, isooctane, methacrolein, methyl methacrylate, butyl rubber, butylated hydroxytoluene, or butylated hydroxyanisole.

In still other embodiments, it relates to methods for preparing isobutene or isoprene as described herein, wherein the olefin mixture is prepared by dehydration of a renewable alcohol mixture comprising one or more renewable $C_4$ or $C_5$ alcohols.

Iso-butanol (2-methyl-1-propanol) has historically found limited applications and its use resembles that of 1-butanol. It has been used as solvent, diluents, wetting agent, cleaner additive and as additive for inks and polymers. Recently, iso-butanol has gained interest as fuel or fuel component as it exhibits a high octane number (Blend Octane R+M/2 is 102-103) and a low vapor pressure (RVP is 3.8-5.2 psi).

Iso-butanol is often considered as a byproduct of the industrial production of 1-butanol (Ullmann's encyclopedia of industrial chemistry, 6$^{th}$ edition, 2002). It is produced from propylene via hydroformylation in the oxo-process (Rh-based catalyst) or via carbonylation in the Reppe-process (Co-based catalyst). Hydroformylation or carbonylation makes n-butanal and iso-butanal in ratios going from 92/8 to 75/25. To obtain iso-butanol, the iso-butanal is hydrogenated over a metal catalyst. Iso-butanol can also be produced from synthesis gas (mixture of CO, $H_2$ and $CO_2$) by a process similar to Fischer-Tropsch, resulting in a mixture of higher alcohols, although often a preferential formation of iso-butanol occurs (Applied Catalysis A, general, 186, p. 407, 1999 and Chemiker Zeitung, 106, p. 249, 1982). Still another route to obtain iso-butanol, is the base-catalysed Guerbet condensation of methanol with ethanol and/or propanol (J. of Molecular Catalysis A: Chemical 200, 137, 2003 and Applied Biochemistry and Biotechnology, 113-116, p. 913, 2004).

Recently, new biochemical routes have been developed to produce selectively iso-butanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (Nature, 451, p. 86, 2008 and US patent 2008/0261230). Recombinant microorganisms are required to enhance the flux of carbon towards the synthesis of 2-keto-acids. In the valine biosynthesis 2-ketoisovalerate is on intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into iso-butanol.

Of the described routes towards iso-butanol above, the Guerbet condensation, the synthesis gas hydrogenation and the 2-keto acid pathway from carbohydrates are routes that can use biomass as primary feedstock. Gasification of biomass results in synthesis gas that can be converted into methanol or directly into iso-butanol. Ethanol is already at very large scale produced by fermentation of carbohydrates or via direct fermentation of synthesis gas into ethanol. So methanol and ethanol resourced from biomass can be further condensed to iso-butanol. The direct 2-keto acid pathway can produce iso-butanol from carbohydrates that are isolated from biomass. Simple carbohydrates can be obtained from plants like sugar cane, sugar beet. More complex carbohydrates can be obtained from plants like maize, wheat and other grain bearing plants. Even more complex carbohydrates can be isolated from substantially any biomass, through unlocking of cellulose and hemicellulose from lignocelluloses.

It is the object of the present invention to use of iso-butanol for the production of isoprene by condensation with formaldehyde. Without willing to be bound to any theory, it is believed that the t-butyl-carbocation is the reactive specie that attacks formaldehyde and that its presence in the aqueous solution where resides also the acid catalyst and the formaldehyde is essential for high reaction rates for the selective condensation reaction. The decomposition of iso-butanol is significantly slower than that of t-butanol under the reaction conditions and as a consequence iso-butanol will serve as efficient solvent that improves the solubility of iso-butene and enhances the presence of t-butyl-carbocations in the aqueous phase. t-Butanol tends to dehydrate too fast so that most of the iso-butene escapes from the aqueous reaction medium and hence a lot of recycling is required.

The following reactions occur under the reaction conditions:

Dehydration:

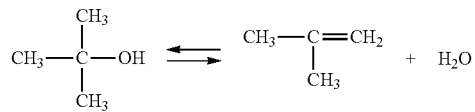

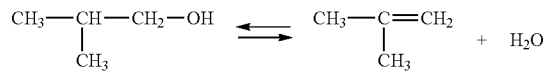

Condensation:

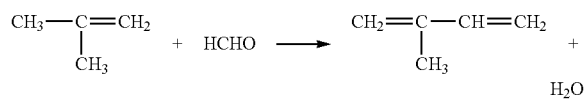

It is the object of the present invention to produce isoprene by reacting formaldehyde with an iso-butene producing alcohol comprising isobutanol.

BRIEF SUMMARY OF THE INVENTION

The present invention is a process to make isoprene comprising:
  a) providing a reaction zone comprising an acidic aqueous solution,
  b) introducing, continuously or intermittently, in said reaction zone
a mixture comprising (I) isobutanol and optionally (ii) t-butanol or an iso-butene precursor which is not isobutanol and not t-butanol or iso-butene or any combination of two or three of these (ii) components,
an aqueous solution of formaldehyde,
  c) operating said reaction zone at conditions effective to dehydrate isobutanol and optionally (ii) t-butanol and optionally the iso-butene precursor to iso-butene and produce isoprene by reaction of formaldehyde and iso-butene while distilling away a mixture comprising produced isoprene, water, unreacted starting materials and other low boiling point components from this reaction zone to the outside of the reaction zone.

An isobutene precursor which is not isobutanol and not t-butanol is a component which is decomposed to isobutene under the above reaction conditions. One can cite ethers.

In another embodiment isobutanol provides 10% or more of the iso-butene for the isoprene synthesis.

In another embodiment isobutanol provides 20% or more of the iso-butene for the isoprene synthesis.

In another embodiment isobutanol provides 30% or more of the iso-butene for the isoprene synthesis.

In another embodiment isobutanol provides 40% or more of the iso-butene for the isoprene synthesis.

In another embodiment isobutanol provides 50% to 100% of the iso-butene for the isoprene synthesis.

DETAILED DESCRIPTION OF THE INVENTION

As regards the feedstock, iso-butanol whereby, advantageously, at least 25 mole % of the carbon is obtained from renewable resources, is a part of the feedstock of the presence invention. Iso-butanol can be produced (i) by Guerbet condensation of methanol with ethanol or propanol, (ii) by direct hydrogenation of carbon monoxide with hydrogen or (iii) by direct biosynthesis via 2-Keto acids, intermediates in amino acid biosynthesis pathways or (iv) by hydroformylation of propylene with a mixture of carbon monoxide and hydrogen. The iso-butene reacting with formaldehyde comes for at least 10% from iso-butanol; the remaining part of the iso-butene reacted with formaldehyde comes from t-butanol, other iso-butene precursor or from fresh iso-butene as feedstock. As regards the iso-butene precursor which is not the isobutanol and not the t-butanol one can cite methyl-t-butyl ether, di-isobutyl-ether, di-t-butyl-ether, ethyl-t-butyl ether and the like, which are decomposed to iso-butene under reaction conditions.

The formaldehyde can be any commercially available form of formaldehyde, most preferable an aqueous solution of formaldehyde.

As regards of the condensation reaction, reacting iso-butene with formaldehyde to make isoprene is know per se. Iso-butene reacts with formaldehyde to give 4,4-dimethyl-m-dioxane which decomposes to isoprene. Said route is described, by way of example, in GB 1370899 and U.S. Pat. No. 3,972,955, the content of which is incorporated by reference in the present application. By way of example, EP 106323 A1, EP 1614671 A1 and EP 2157072 A1, the content of which is incorporated by reference in the present application, describe a route in which iso-butene or t-butanol is reacted with formaldehyde in acidic aqueous medium to produce isoprene. The operating conditions described in the above cited prior art can be used in the present invention.

In an embodiment the operating conditions and the catalyst are optimised such that directly isoprene is produced. The process is catalysed by acid catalysts. The operating conditions are chosen such that the isoprene is removed as quickly as possible form the reaction mixture upon its formation. This is generally being done by vaporisation of the formed isoprene together with non-converted iso-butene and water vapour. An appropriate control of the reactor pressure will determine the boiling off of the reaction products and other entrained components present in the reactor. The reactor pressure is from 7 to 18 bars, preferably from 8 to 15 bars gauge. The reaction temperature is from 140 to 240° C., preferably from 160 to 220° C. These vapours are condensed and the isoprene is isolated from the remaining iso-butene and an aqueous phase. The iso-butene (as fresh feed or as dehydration product of iso-butanol or t-butanol or coming from the iso-butene precursor), iso-butene precursor, iso-butanol and t-butanol can be recycled back into the conversion reactor. So the t-butyl-moieties in the reactor are coming from fresh feed composed of iso-butanol, t-butanol, iso-butene precursor and iso-butene, although the t-butyl-moiety can also originate from the recycled iso-butene, recycled t-butanol, recycled iso-butene precursor and recycled iso-butanol. The isolated isoprene is typically very pure after distillation as no other hydrocarbons with five carbons can be produced out of iso-butanol/t-butanol/iso-butene and formaldehyde. Typical byproducts are oligomers of isoprene and formaldehyde that are easy to separate from isoprene.

The catalyst may be any acid, homogeneous or heterogeneous. It is preferred that the catalyst is a high boiling acid that remains in the aqueous phase of the reactor and does not vaporises with the isoprene out of the reactor vessel. Examples of liquid homogeneous catalysts are sulphuric acid, hydrosulfuric acid, phosphoric acid, monohydrophosphoric acid, dihydrophosphoric acid, boric acid, nitric acid, methanesulfonic acid, para-toluyl-sulfonic acid, heteropolyacids etc. Heterogeneous acids may also be use, among others sulfonated crosslinked divinylstyrene, sulfonated polyfluorohydrocarbons, sulfonated amorphous silica's, sulfonated mesoporous silica's, sulfonated zirconia's, supported heteropolyacids, zeolites etc.

The condensation reaction can be carried out in various reactor configurations: (i) batch stirred tank reactors, (ii) continuous stirred tank reactors, (iii) jet type or siphon type circulating reactors and (iv) bubble column reactors. It is essential that a good mixing of the reactants occurs as otherwise the local ratio of t-butyl-moieties to formaldehyde might be non-optimal and hence resulting in different reactions pathways resulting in loss of selectivity. The molar ratio of t-butyl-moiety (as the molar sum of fresh iso-butanol, t-butanol, iso-butene precursor or iso-butene) send as fresh feed to the reactor to formaldehyde send as fresh feed to the reactor is from 0.5 to 2, preferably close to 1. The molar ratio of t-butyl-moiety (as the molar sum of fresh iso-butanol, fresh t-butanol, fresh iso-butene, fresh iso-butene precursor, recycled iso-butanol, recycled t-butanol, recycled iso-butene precursor or recycled iso-butene) to formaldehyde in the reactor is from 1 to 18, preferably from 1.5 to 5, most preferably from 2 to 4. Should the iso-butene precursor leads to 2 or 3 moles iso-butene, the number of moles of isobutene precursor has to be multiply by 2 or 3 in the above ratios of t-butyl-moiety to formaldehyde.

The invention claimed is:

1. A process to make isoprene comprising:
   a) providing a reaction zone comprising an acidic aqueous solution,
   b) introducing, continuously or intermittently, in said reaction zone a mixture comprising isobutanol, t-butanol, and an aqueous solution of formaldehyde,
   c) operating said reaction zone at conditions effective to dehydrate the isobutanol and the t-butanol to iso-butene and,
   d) reacting formaldehyde and iso-butene to produce isoprene while distilling away a mixture comprising produced isoprene, water, unreacted starting materials and other low boiling point components from the reaction zone to the outside of the reaction zone.

2. The process according to claim 1, wherein isobutanol provides 10% or more of the iso-butene for the isoprene synthesis.

3. The process according to claim 1, wherein isobutanol provides 20% or more of the iso-butene for the isoprene synthesis.

4. The process according to claim 1, wherein isobutanol provides 30% or more of the iso-butene for the isoprene synthesis.

5. The process according to claim 1, wherein isobutanol provides 40% or more of the iso-butene for the isoprene synthesis.

6. The process according to claim 1, wherein isobutanol provides 50% to 100% of the iso-butene for the isoprene synthesis.

7. The process according to claim 1, wherein the reaction zone pressure is from 7 to 18 bars gauge.

8. The process according to claim 1, wherein the reaction zone pressure is from 8 to 15 bars gauge.

9. The process according to claim 1, wherein the reaction zone temperature is from 140 to 240° C.

10. The process according to claim 1, wherein the reaction zone temperature is from 160 to 220° C.

11. The process according to claim 1, wherein a molar ratio of t-butyl-moiety sent as fresh feed to the reaction zone to formaldehyde sent as fresh feed to the reaction zone is from 0.5 to 2.

12. The process according to claim 11, wherein the molar ratio of t-butyl-moiety sent as fresh feed to the reaction zone to formaldehyde sent as fresh feed to the reaction zone is close to 1.

13. The process according to claim 1, wherein a molar ratio of t-butyl-moiety to formaldehyde in the reactor reaction zone is from 1 to 18.

14. The process according to claim 13, wherein the molar ratio of t-butyl-moiety to formaldehyde in the reaction zone is from 1.5 to 5.

15. The process according to claim 14, wherein the molar ratio of t-butyl-moiety to formaldehyde in the reaction zone is from 2 to 4.

16. The process according to claim 1, wherein the mixture further comprises an iso-butene precursor that is an ether, and wherein the reaction zone is operated at conditions effective to decompose the iso-butene precursor to iso-butene, dehydrate the isobutanol to iso-butene, and produce isoprene by reaction of formaldehyde and iso-butene while distilling away the mixture comprising produced isoprene, water, unreacted starting materials and other low boiling point components from this reaction zone to the outside of the reaction zone.

17. The process according to claim 16, wherein the ether is ethyl-t-butyl ether, di-isobutyl-ether, di-t-butyl-ether, or ethyl-t-butyl ether.

18. The process according to claim 1, wherein the mixture further comprises iso-butene, and wherein the reaction zone is operated at conditions effective to dehydrate the isobutanol to iso-butene and produce isoprene by reaction of formaldehyde and iso-butene while distilling away the mixture comprising produced isoprene, water, unreacted starting materials and other low boiling point components from this reaction zone to the outside of the reaction zone.

19. A process to make isoprene comprising:
   providing a reaction zone comprising an acidic aqueous solution;
   introducing, continuously or intermittently, in said reaction zone a mixture comprising isobutanol, t-butanol, and an aqueous solution of formaldehyde; and
   operating said reaction zone at conditions effective to dehydrate the isobutanol and t-butanol to iso-butene, operating said reaction zone to iso-butene, and
   reacting formaldehyde and iso-butene to produce isoprene while distilling away a mixture comprising produced isoprene and water from the reaction zone to outside of the reaction zone, wherein isobutanol provides 10% or more of the iso-butene for the isoprene synthesis, and wherein under the reaction conditions in the reaction zone the iso-butanol acts as solvent to improve solubility of iso-butene and enhance the presence of t-butyl-carbocations in the aqueous phase.

* * * * *